(12) United States Patent
Olsen et al.

(10) Patent No.: US 8,945,179 B2
(45) Date of Patent: Feb. 3, 2015

(54) SINGLE DISC OCCLUSIONARY PATENT FORAMEN OVALE CLOSURE DEVICE

(71) Applicant: Cordis Corporation, Bridgewater, NJ (US)

(72) Inventors: Daniel Olsen, Califon, NJ (US); Randy David B. Grishaber, Danville, CA (US); Chao-Chin Chen, Edison, NJ (US); Rudy Cedro, Clinton, NJ (US); John O'Brien, Piscataway, NJ (US)

(73) Assignee: Cordis Corporation, Fremont, CA (US)

( * ) Notice: Subject to any disclaimer, the term of this patent is extended or adjusted under 35 U.S.C. 154(b) by 0 days.

(21) Appl. No.: 13/795,838

(22) Filed: Mar. 12, 2013

(65) Prior Publication Data

US 2013/0190811 A1    Jul. 25, 2013

Related U.S. Application Data

(62) Division of application No. 11/761,123, filed on Jun. 11, 2007, now abandoned.

(60) Provisional application No. 60/804,376, filed on Jun. 9, 2006.

(51) Int. Cl.
*A61B 17/08* (2006.01)
*A61B 17/00* (2006.01)
*A61B 17/04* (2006.01)

(52) U.S. Cl.
CPC ... *A61B 17/0057* (2013.01); *A61B 2017/00575* (2013.01); *A61B 2017/00579* (2013.01); *A61B 2017/00592* (2013.01); *A61B 2017/00615* (2013.01); *A61B 2017/00862* (2013.01);
(Continued)

(58) Field of Classification Search
USPC ............... 606/151, 157, 158, 200, 213, 215; 623/23.72
See application file for complete search history.

(56) References Cited

U.S. PATENT DOCUMENTS 3,874,388 A * 4/1975 King et al. .............. 606/232
5,342,393 A * 8/1994 Stack ...................... 606/213
5,350,399 A    9/1994 Erlebacher et al.
(Continued)

FOREIGN PATENT DOCUMENTS

WO   WO 01/21247 A    3/2001
WO   WO 2004/100803 A    11/2004

OTHER PUBLICATIONS

International Search Report in corresponding PCT/US2007/070874 dated Nov. 27, 2007.

*Primary Examiner* — Melanie Tyson
*Assistant Examiner* — Alexander Orkin

(57) ABSTRACT

Described are method and device for closing a passageway in a body, for example a patent foramen ovale (PFO) in a heart, and related methods of using such closure devices for closing the passageway. The method includes locating a distal end of a closure device adjacent to the passageway. The closure device may include a closure line with proximal and distal ends, an expandable tissue anchor located along the distal end of the closure line, and an expandable occluder member located along the proximal end of the closure line. The expandable tissue anchor is deployed into tissue adjacent to the passageway. The expandable occluder member is deployed adjacent to the passageway such that the expandable occluder member substantially covers the second opening to the passageway.

3 Claims, 15 Drawing Sheets

(52) U.S. Cl.
CPC . *A61B2017/0412* (2013.01); *A61B 2017/0437* (2013.01); *A61B 2017/0464* (2013.01)
USPC ....................................... 606/213; 623/23.72

(56) References Cited

U.S. PATENT DOCUMENTS

| | | | |
|---|---|---|---|
| 5,370,661 A | 12/1994 | Branch | |
| 5,853,422 A | 12/1998 | Huebsch et al. | |
| 5,944,738 A | 8/1999 | Amplatz et al. | |
| 6,689,150 B1 | 2/2004 | VanTassel et al. | |
| 7,618,449 B2 * | 11/2009 | Tremulis et al. | 623/2.11 |
| 2002/0183787 A1 | 12/2002 | Wahr et al. | |
| 2003/0018358 A1 * | 1/2003 | Saadat | 606/232 |
| 2003/0144694 A1 | 7/2003 | Chanduszko et al. | |
| 2003/0163191 A1 | 8/2003 | Nikolic et al. | |
| 2003/0171774 A1 | 9/2003 | Freudenthal et al. | |
| 2004/0044364 A1 | 3/2004 | DeVries et al. | |
| 2004/0092973 A1 * | 5/2004 | Chanduszko et al. | 606/151 |
| 2004/0220596 A1 | 11/2004 | Frazier et al. | |
| 2005/0043759 A1 | 2/2005 | Chanduszko | |
| 2005/0059984 A1 | 3/2005 | Chanduszko et al. | |
| 2005/0075654 A1 * | 4/2005 | Kelleher | 606/151 |
| 2005/0119675 A1 | 6/2005 | Adams et al. | |
| 2005/0149115 A1 * | 7/2005 | Roue et al. | 606/213 |
| 2005/0256532 A1 | 11/2005 | Nayak et al. | |
| 2006/0030881 A1 | 2/2006 | Sharkey et al. | |

* cited by examiner

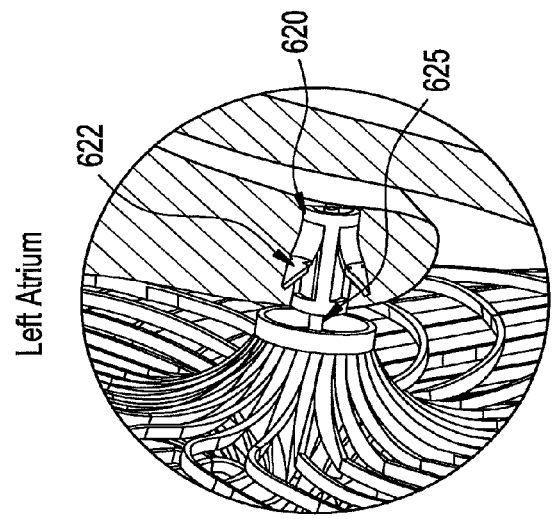
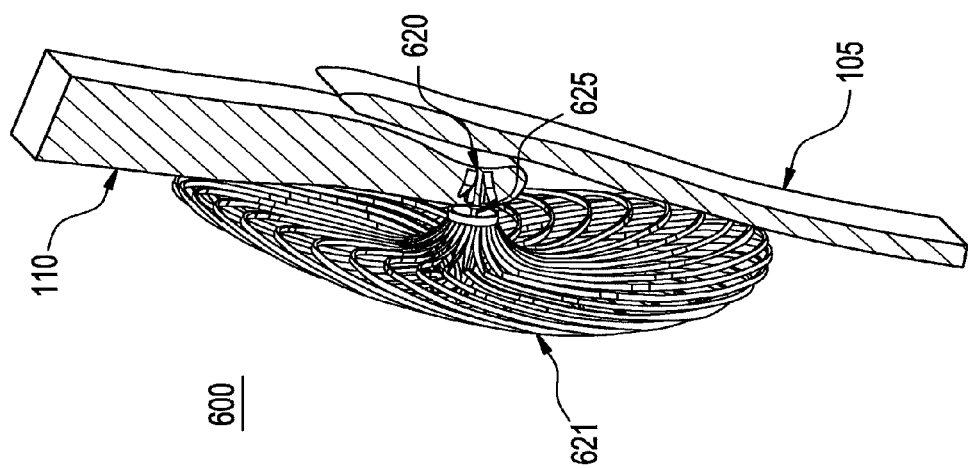

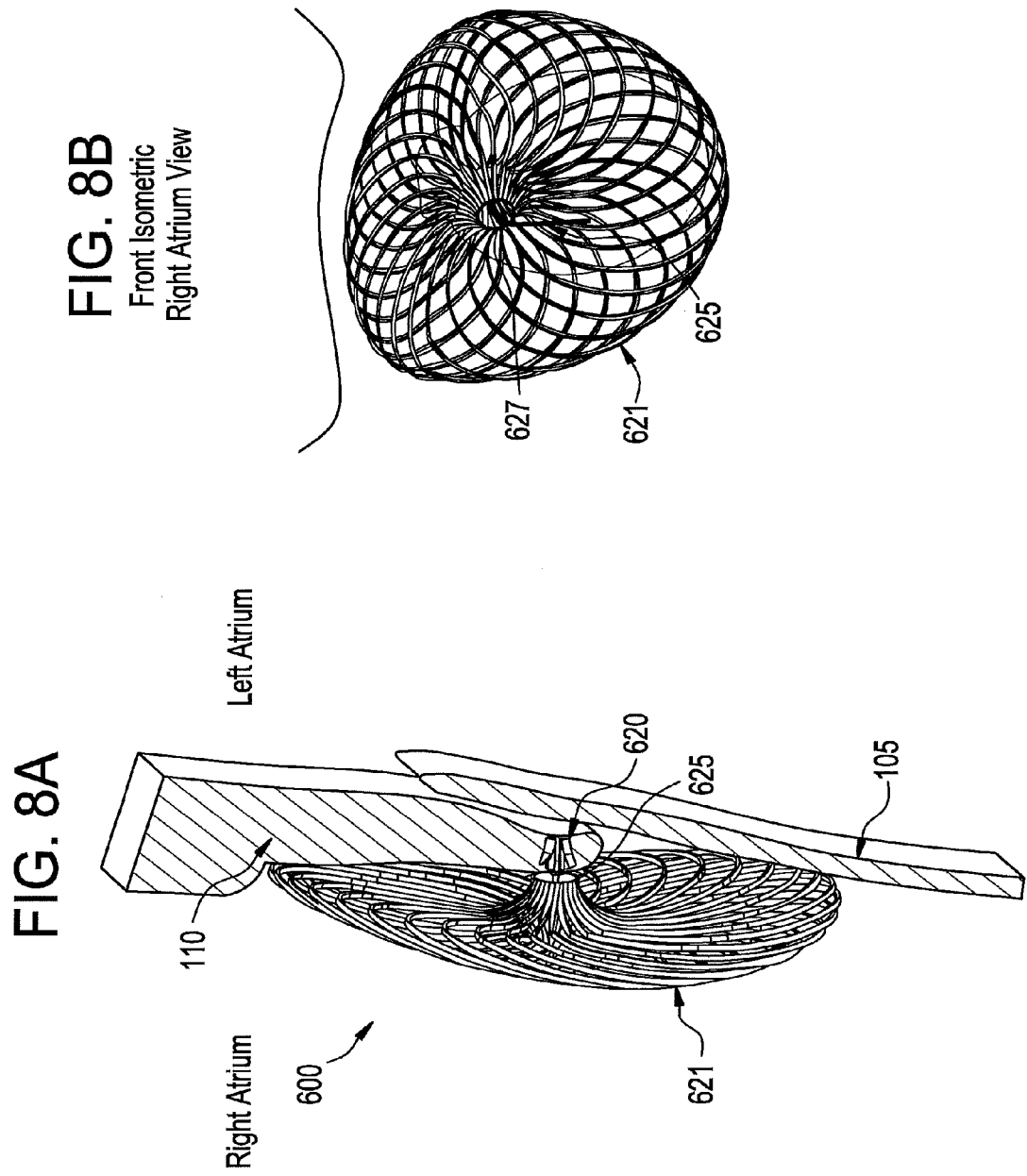

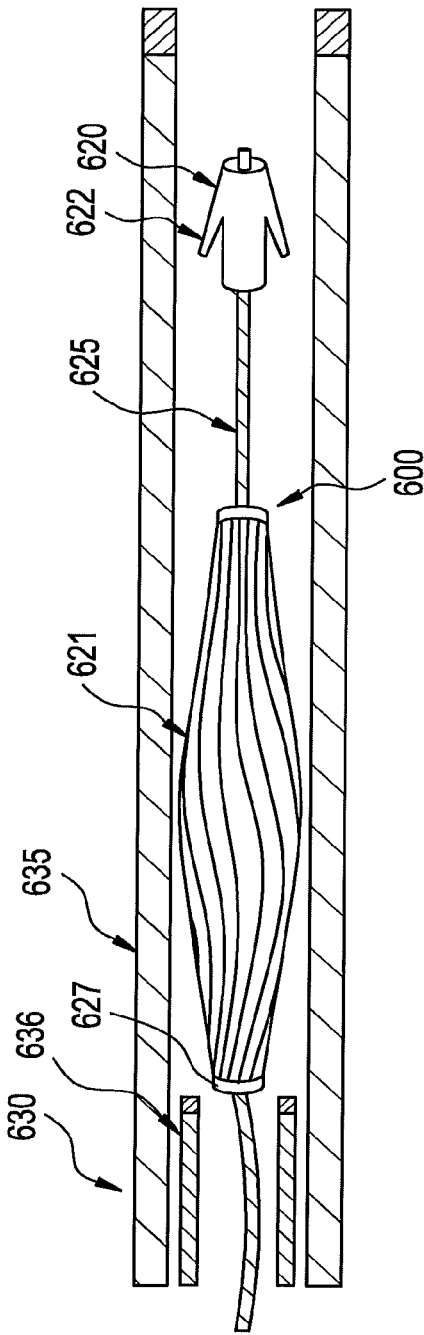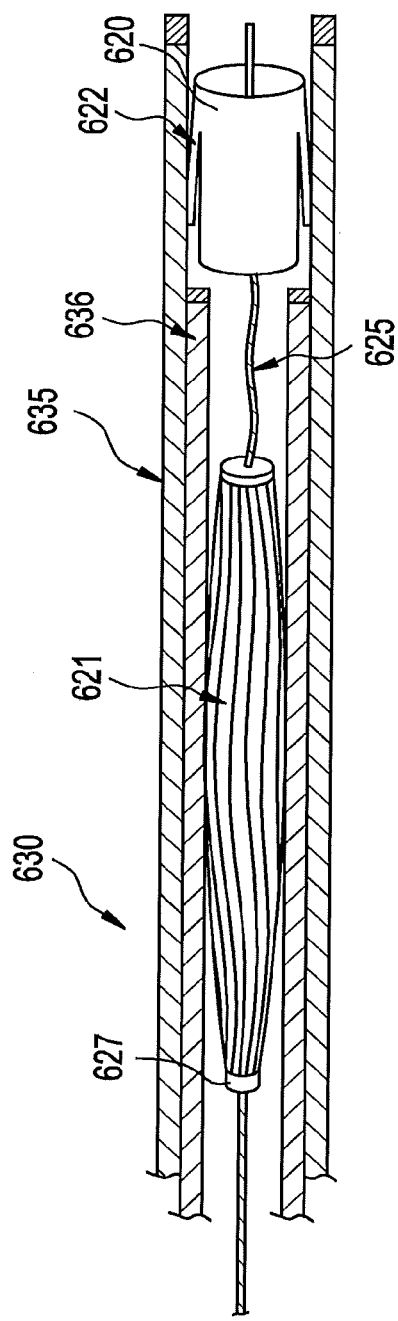

Right Atrium

SINGLE DISC OCCLUSIONARY PATENT FORAMEN OVALE CLOSURE DEVICE

CROSS-REFERENCE TO RELATED APPLICATION

This application is a divisional of U.S. application Ser. No. 11/761,123 filed on Jun. 11, 2007, which claims the benefit of U.S. Provisional Application Ser. No. 60/713,388 filed on Sep. 1, 2005. The complete disclosure of the aforementioned related U.S. patent applications are hereby incorporated by reference herein.

This application claims the benefit of U.S. Provisional Application Ser. No. 60/804,376, filed Jun. 9, 2006, which is incorporated by reference herein.

FIELD OF THE INVENTION

This invention relates to devices for closing a passageway in a body, for example a patent foramen ovale (PFO) in a heart, and related methods of using such closure devices for closing the passageway.

BACKGROUND OF THE INVENTION

Patent foramen ovale (PFO) is an anatomical interatrial communication with potential for right-to-left shunting of blood. Foramen ovale has been known since the time of Galen. In 1564, Leonardi Botali, an Italian surgeon, was the first to describe the presence of foramen ovale at birth. However, the function of foramen ovale in utero was not known at that time. In 1877, Cohnheim described paradoxical embolism in relation to patent foramen ovale.

Patent foramen ovale is a flap-like opening between the atrial septa primum and secundum at the location of the fossa ovalis that persists after age one year. In utero, the foramen ovale serves as a physiologic conduit for right-to-left shunting of blood in the fetal heart. After birth, with the establishment of pulmonary circulation, the increased left atrial blood flow and pressure presses the septum primum (SP) against the walls of the septum secundum (SS), covering the foramen ovale and resulting in functional closure of the foramen ovale. This closure is usually followed by anatomical closure of the foramen ovale due to fusion of the septum primum (SP) to the septum secundum (SS).

Where anatomical closure of the foramen ovale does not occur, a patent foramen ovale (PFO) is created. A patent foramen ovale is a persistent, usually flap-like opening between the atrial septum primum (SP) and septum secundum (SS) of a heart. A patent foramen ovale results when either partial or no fusion of the septum primum (SP) to the septum secundum (SS) occurs. In the case of partial fusion or no fusion, a persistent passageway (PFO track) exists between the septum primum (SP) and septum secundum (SS). This opening or passageway is typically parallel to the plane of the septum primum, and has a mouth that is generally oval in shape. Normally the opening is relatively long, but quite narrow. The opening may be held closed due to the mean pressure in the left atrium (LA) being typically higher than in the right atrium (RA). In this manner, the septum primum acts like a one-way valve, preventing fluid communication between the right and left atria through the PFO track. However, at times, the pressure may temporarily be higher in the right atrium, causing the PFO track to open up and allow some fluid to pass from the right atrium to the left atrium. Although the PFO track is often held closed, the endothelialized surfaces of the tissues forming the PFO track prevent the tissues from healing together and permanently closing the PFO track.

Studies have shown that a relatively large percentage of adults have a patent foramen ovale (PFO). It is believed that embolism via a PFO may be a cause of a significant number of ischemic strokes, particularly in relatively young patients. It has been estimated that in 50% of cryptogenic strokes, a PFO is present. Blood clots that form in the venous circulation (e.g., the legs) can embolize, and may enter the arterial circulation via the PFO, subsequently entering the cerebral circulation, resulting in an embolic stroke. Blood clots may also form in the vicinity of the PFO, and embolize into the arterial circulation and into the cerebral circulation. Patients suffering a cryptogenic stroke or a transient ischemic attack (TIA) in the presence of a PFO often are considered for medical therapy to reduce the risk of a recurrent embolic event.

Pharmacological therapy often includes oral anticoagulants or antiplatelet agents. These therapies may lead to certain side effects, including hemorrhage. If pharmacologic therapy is unsuitable, open heart surgery may be employed to close a PFO with stitches, for example. Like other open surgical treatments, this surgery is highly invasive, risky, requires general anesthesia, and may result in lengthy recuperation.

Nonsurgical closure of a PFO is possible with umbrella-like devices developed for percutaneous closure of atrial septal defects (ASD) (a condition where there is not a well-developed septum primum (SP)). Many of these conventional devices used for ASD, however, are technically complex, bulky, and difficult to deploy in a precise location. In addition, such devices may be difficult or impossible to retrieve and/or reposition should initial positioning not be satisfactory. Moreover, these devices are specially designed for ASD and therefore may not be suitable to close and seal a PFO, particularly because the septum primum (SP) overlaps the septum secundum (SS).

SUMMARY OF THE INVENTION

The present invention relates to devices for closing a passageway in a body, for example a patent foramen ovale (PFO) in a heart, and related methods of using such closure devices for closing the passageway. The closure device includes a closure line having a first and a second end. A first expandable member is connected to the first end of the closure line. A second expandable member is located along the second end of the closure line, and is capable of sliding along the closure line in one direction while preventing sliding movement in the opposite direction. Alternatively the second expandable member is fixed along the second end of the closure line.

Another embodiment of the invention includes a closure line having a first and a second end. An expandable tissue anchor is connected to the first end of the closure line, the tissue anchor being adapted to pierce into tissue within close approximation to the passageway and subsequently expand to embed into the tissue. An expandable flow occluder is located along the second end of the closure line, the expandable flow occluder having a locking mechanism integrated therein. The locking mechanism allows the closure line to uni-axially slide through the expandable flow occluder in one direction, and prevent sliding movement in the opposite direction.

Another embodiment of the invention includes a method for closing a passageway in a body, the passageway having a first and a second open end. The method includes locating a distal end of a closure device adjacent to the passageway, the closure device having a closure line with proximal and distal ends, an expandable tissue anchor located along the distal end of the closure line, and an expandable occluder member located along the proximal end of the closure line. The expandable tissue anchor is deployed into tissue adjacent to the passageway. The expandable occluder member is deployed adjacent to the passageway such that the expandable occluder member substantially covers the second opening to the passageway.

BRIEF DESCRIPTION OF THE DRAWINGS

FIG. 6A illustrates the closure device deployed with the distal anchor member in the septum secundum, and the proximal occluder member against the septum primum and septum secundum substantially occluding the PFO track, according to one embodiment of the present invention.

FIG. 6B is a close-up perspective view illustrating the relationship between the distal anchor member, the closure line and the proximal occluder member according to one embodiment of the present invention.

FIG. 8A is a perspective view illustrating one an asymmetric proximal occluder member according to one embodiment of the present invention.

FIG. 8B is a close-up perspective view illustrating an asymmetric proximal occluder member according to one embodiment of the present invention.

FIG. 10A is a section view illustrating the closure device 600 loaded into a delivery device 630 according to one embodiment of the present invention.

FIG. 10B is a section view illustrating the closure device 600 loaded into a delivery device 630 according to another embodiment of the present invention.

DETAILED DESCRIPTION OF THE INVENTION

The various figures show embodiments of the patent foramen ovale (PFO) closure device and methods of using the device to close a PFO. The device and related methods are described herein in connection with mechanically closing a PFO. These devices, however, also are suitable for closing other openings or passageways, including other such openings in the heart, for example atrial septal defects, ventricular septal defects, and patent ducts arterioses, as well as openings or passageways in other portions of a body such as an arteriovenous fistula. The invention therefore is not limited to use of the inventive closure devices to close PFO's.

A human heart has four chambers. The upper chambers are called the left and right atria, and the lower chambers are called the left and right ventricles. A wall of muscle called the septum separates the left and right atria and the left and right ventricles. That portion of the septum that separates the two upper chambers (the right and left atria) of the heart is termed the atrial (or interatrial) septum while the portion of the septum that lies between the two lower chambers (the right and left ventricles) of the heart is called the ventricular (or interventricular) septum.

Figure 1:
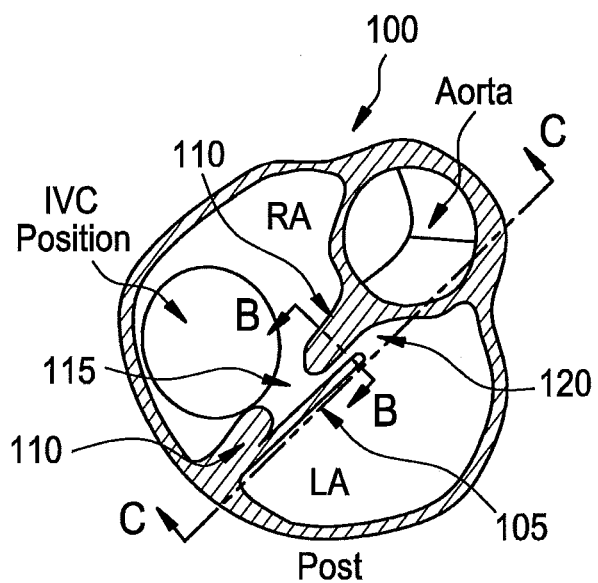
FIG. 1 is a short axis view of the heart at the level of the right atrium (RA) and the left atrium (LA), in a plane generally parallel to the atrio-ventricular groove, and at the level of the aortic valve, showing a PFO track.

FIG. 1 illustrates a short-axis view of the heart 100 at the level of the right atrium (RA) and left atrium (LA), in a plane generally parallel to the atrio-ventricular groove, and at the level of the aortic valve. This view is looking from caudal to cranial. FIG. 1 also shows the septum primum (SP) 105, a flap-like structure, which normally covers the foramen ovale 115, an opening in the septum secundum (SS) 110 of the heart 100. In utero, the foramen ovale 115 serves as a physiologic conduit for right-to-left shunting of blood in the fetal heart. After birth, with the establishment of pulmonary circulation, the increased left atrial blood flow and pressure presses the septum primum (SP) 105 against the walls of the septum secundum (SS) 110, covering the foramen ovale 115 and resulting in functional closure of the foramen ovale 115. This closure is usually followed by anatomical closure of the foramen ovale 115 due to fusion of the septum primum (SP) 105 to the septum secundum (SS) 110.

Figure 2:
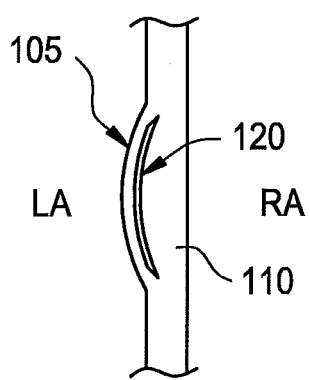
FIG. 2 is a cross-sectional view of the PFO track of FIG. 1 in a closed configuration.
Figure 4A:
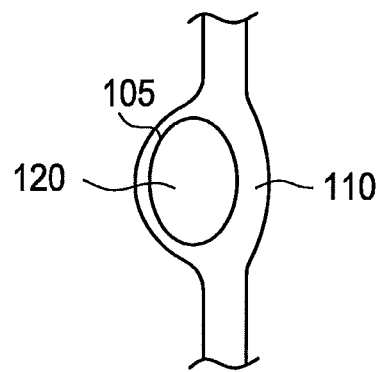
FIG. 4A is a cross-sectional view of the PFO track of FIG. 2 in an open configuration.
Figure 3:
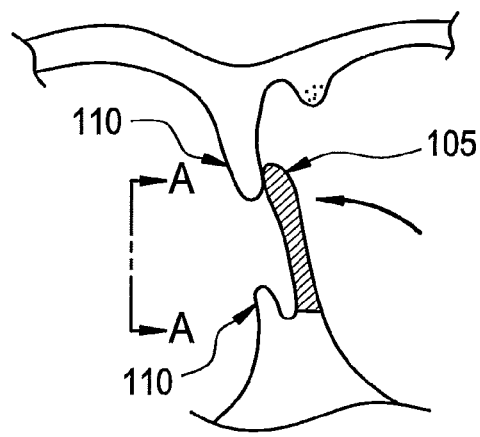
FIG. 3 is a close-up section view illustrating the PFO track held in the closed position by left atrial pressure.
Figure 4B:
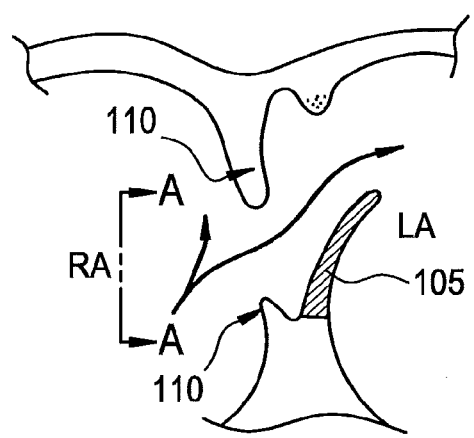
FIG. 4B is a close-up section view illustrating the PFO track in an open configuration.

The PFO results when either partial or no fusion of the septum primum 105 to the septum secundum 110 occurs. When this condition exists, a passageway (PFO track) 120 between the septum primum 105 and septum secundum 110 may allow communication of blood between the atria. This PFO track 120 is typically parallel to the plane of the septum primum 105, and has an opening that is generally oval in shape. FIG. 2 illustrates the opening of the PFO track 120 as viewed from an end of the track. Normally the opening is relatively tall, but quite narrow. The opening may be held closed by the mean pressure in the left atrium, which is typically higher than the right atrium. FIG. 3 is a close-up section view of the PFO track 120 held in the closed position by left atrial pressure. In this position, the septum primum 105 acts like a one-way valve, preventing fluid communication between the right and left atria through the PFO track 120. Occasionally, the pressure in the right atrium may temporarily be higher than the left atrium. When this condition occurs, the PFO track 120 opens and allow some fluid to pass from the right atrium to the left atrium, as indicated in FIGS. 4A and 4B. In particular, FIG. 4A is a cross-sectional view showing the PFO track of FIG. 2 in an open configuration. Similarly, FIG. 4B is a close-up section view illustrating the PFO track in an open configuration.

Figure 5D:
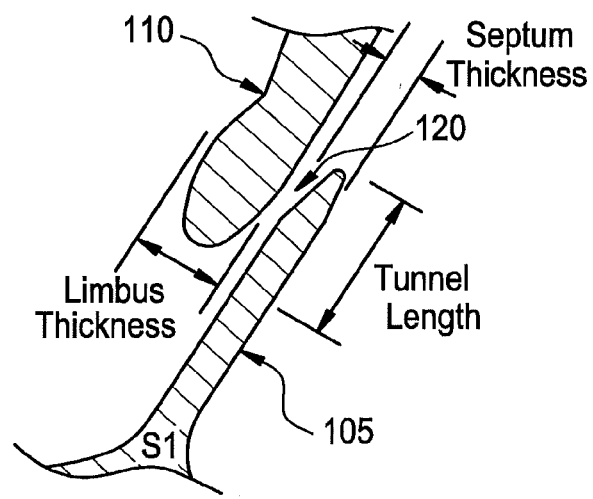
FIG. 5D is a close-up section view of the PFO track, showing the tunnel formed by the tissue extension.
Figure 5A:
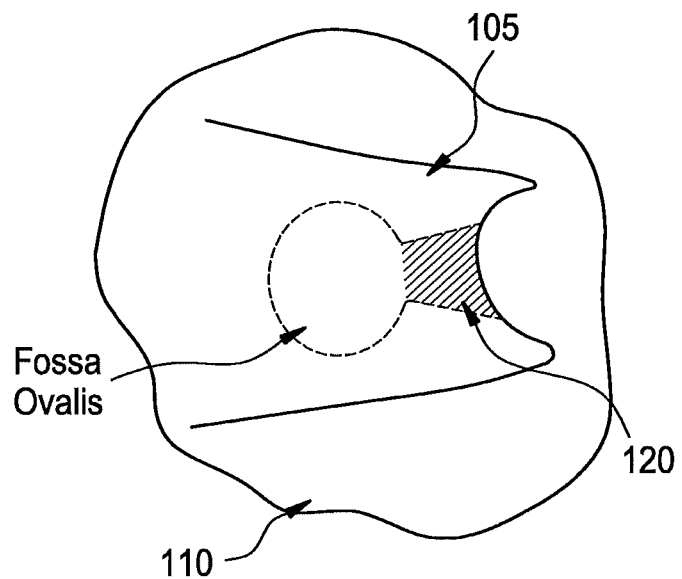
FIG. 5A is a cross-sectional view illustrating the PFO tract of FIG. 1.
Figure 5B:
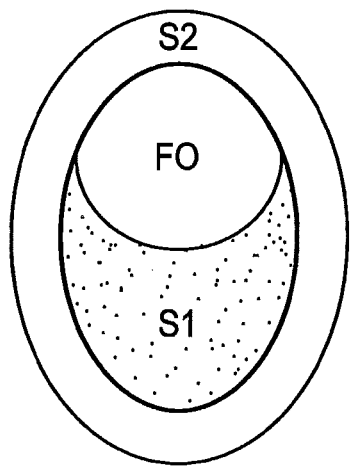
FIG. 5B is a section view taken along line A-A in FIG. 4B.
Figure 5C:
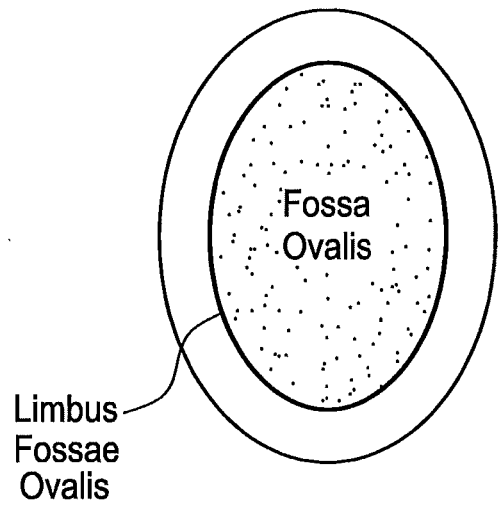
FIG. 5C is a section view taken along line A-A in FIG. 3.

Although the PFO track 120 is often held closed, the endothelialized surfaces of the tissues forming the PFO track 120 prevent the tissue from healing together and permanently closing the PFO track 120. As can be seen in FIGS. 5A-5C, (a view from line "C-C" of FIG. 1), the septum primum 105 is firmly attached to the septum secundum 110 around most of the perimeter of the Fossa Ovalis 115, but has an opening along one side. The septum primum 105 is often connected, as shown, by two or more extensions of tissue along the sides of the PFO track 120 forming a tunnel. FIG. 5D is a magnified section view of the PFO track 120, showing the tunnel formed by the tissue extensions. Typically, the tunnel length in an adult human can range between 2 and 13 mm.

The present invention relates to a system and method for closing a passageway in a body. In a particular embodiment, the device is used to close the Patent Foramen Ovale in a human heart. One of ordinary skill in the art would understand that similar embodiments could be used to close other passageways and openings in the body without departing from the general intent or teachings of the present invention.

FIG. 6A illustrates a device used to close the PFO according to one embodiment of the present invention. The device 600 comprises a flexible closure line 625 coupled to two expandable members, distal anchor member 620 and proximal occluder member 621 respectively. Anchor member 620 is an anchor coupled to the distal end of the closure line 625, while occluder member 621 is an expandable geometric structure coupled to the proximal end of the flexible closure line 625. Occluder member 621 is capable of sliding along closure line 625 and locking in desired location to cinch or take-up slack in closure line 625 length, bringing the proximal occluder member 621 into contact with the septal wall comprised of septum secundum 110 and the septum primum 105 such that blood flow to the PFO tunnel is closed off.

It should be noted that the septum secundum 110 and the septum primum 105 do not have to be touching to effect proper closure of the PFO. Instead, the proximal member 621 occludes flow to the PFO track (tunnel) 120 by substantially covering the tunnel entrance. It should also be noted that the proximal occluder member 621 may or may not be covered with a biocompatible polymeric fabric to assist in substantially occluding blood flow. For a design in which a fabric covering is not used, blood flow would eventually be shunted by the heart's incorporation of the device.

The distal anchor member 620 is a tissue anchor that is delivered into the septum secundum 110 or septum primum 105 via a catheter delivery system and is deployed. Upon deployment, the distal member 620 is anchored into the tissue forming the septum secundum 110 or the septum primum 105 such that the anchor member 620 is immobile and can withstand the pull force needed to properly seat the proximal occluder member 621 against the septal wall without the distal anchor member 620 detaching from the septal tissue.

In one embodiment, the distal anchor member 620 comprises a main body having a needle like tip capable of penetrating the septum (septum secundum 110 and/or the septum primum 105) and one or more barbs 622 that project outward from the main body. The characteristics of the barbs 622 are such that after delivery of the anchor into the septum tissue, the barbs 622 extend outward in a radial direction and prevent the distal anchor member 620 from being withdrawn from the tissue—very similar to the barb integrated into a fish hook.

A locking mechanism 627 is operatively incorporated into the occluder member 621 to secure the occluder member 621 to the closure line 625. In one embodiment, the locking member may be an integral part of the occluder member 621, formed into the hub of the occluder member 621. In another embodiment of the invention, the locking mechanism 627 may be a separate component or member functionally that although is physically a separate member, is functionally integrated with the occluder member 621. That is to say, the locking mechanism 627 can secure to the closure line 625 and prevent relative movement between the closure line 625 and the occluder member 621 when the hub of the occluder member 621 comes in contact with the locking mechanism 627.

Figure 7A:
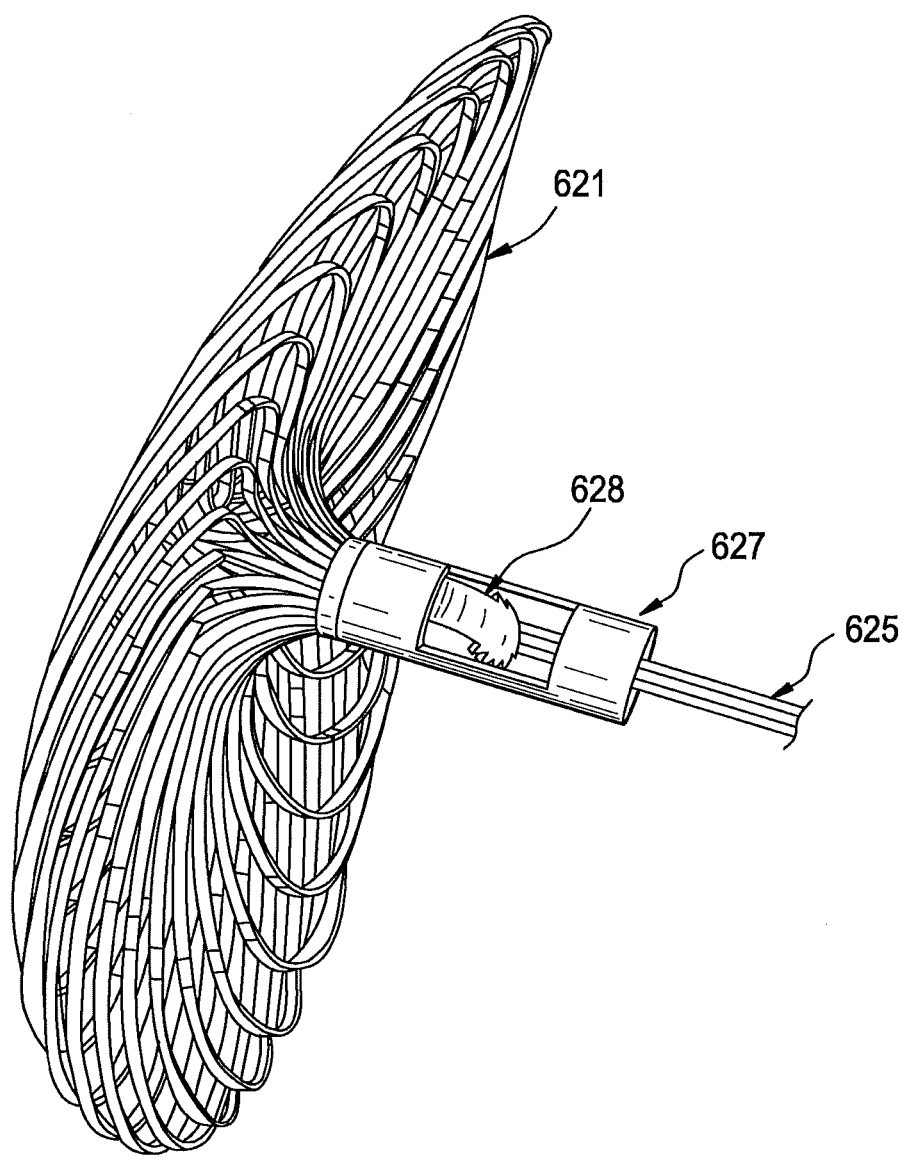
FIG. 7A shows one embodiment of a suture locking device integrated into the occluder member according to one embodiment of the present invention.
Figure 7B:
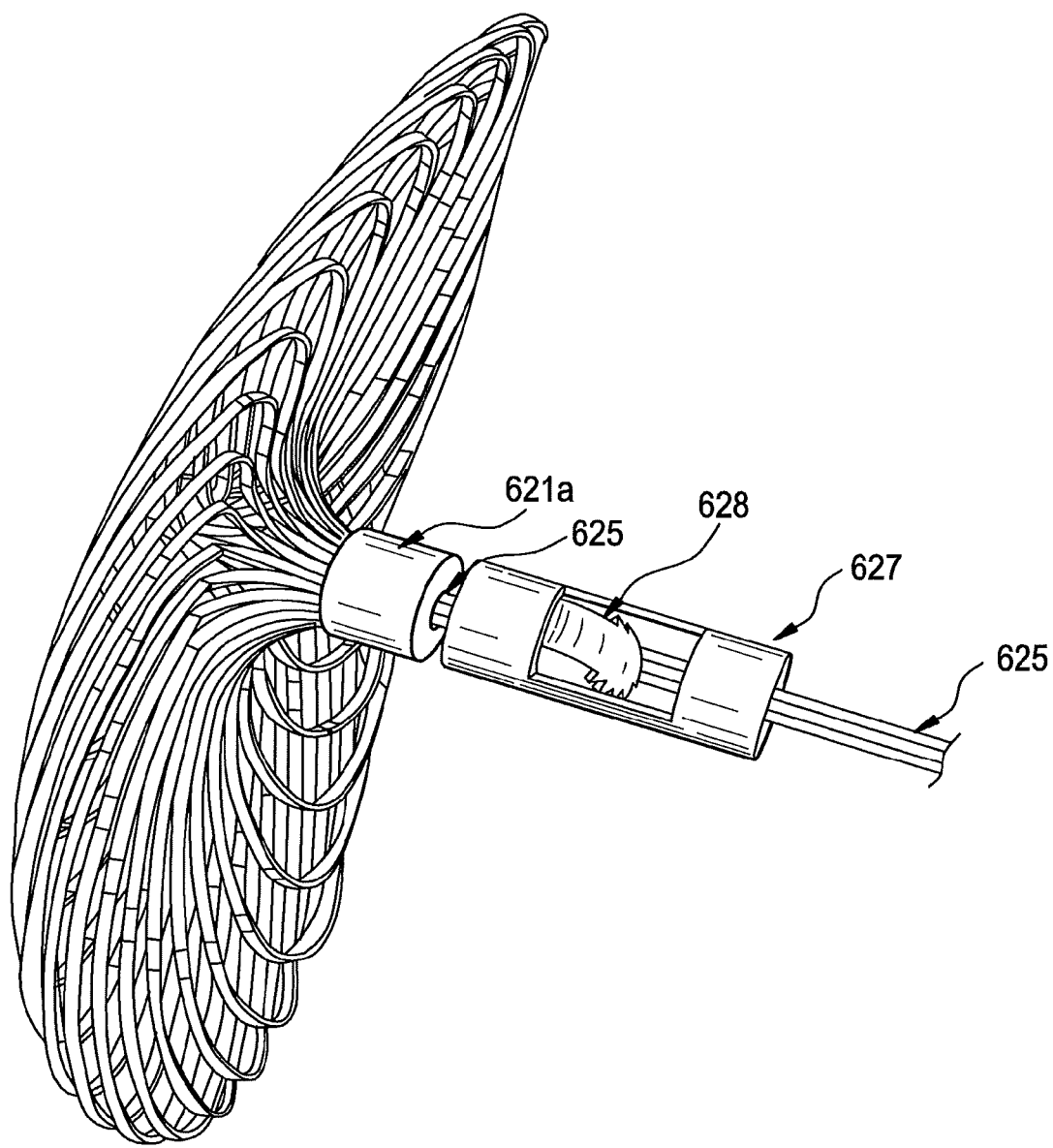
FIG. 7B shows one embodiment of a suture locking device operatively associated with a separate occluder member according to one embodiment of the present invention.

FIG. 7A is an isometric view of an occluder member 621 with a locking mechanism 627 integrated into the occluder member's 621 proximal end. Similarly, FIG. 7B is an isometric view of an occluder member 621 operatively associated with a separate and distinct locking mechanism 627 along a closure line 625. In this embodiment, the locking mechanism 625 secures to the closure line 625, and effectively secures the occluder member 621 relative the closure line 625 when the hub 621a of the occluder member 621 comes in contact with the locking mechanism 627.

In one embodiment, the locking mechanism 627 allows the closure line 625 to slide through occluder member 621 in one direction, and prevent sliding movement in the opposite direction. Examples of functionally similar commercial locking mechanisms include the DePuy Mitek RAPIDLOC™ device; zip ties; and similar linear locking devices known in the art. In a preferred embodiment of the locking mechanism 627, mechanical appendage or tang 628 is used to lock onto the closure line 625 by having small finger-like protrusions that impinge on and push between the individual woven strands of the closure line 625.

Alternatively, the proximal occluder member 621 may be fixed to the closure line 625 at a predetermined distance from anchor member 620. This may particularly be the case when the closure line 625 has an elastic or recoil ability and is capable of exerting tension when deployed, pulling the proximal and distal members 621, 620 together and effectively compressing proximal occluder member 621 against the septal wall inside the right atrium of the heart. In still a further embodiment of the invention, a closure device 600 may include an elastic closure line 625 and a slideable proximal occluder member 621. In this embodiment, the occluder member 621 is capable of allowing the flexible closure line 625 to slide through the occluder member 621 in one direction, and prevent sliding movement in the opposite direction, while the closure line 625 exerts tension between the proximal and distal members 621, 620 respectively. These configurations should not necessarily be considered limiting, and other combinations of components are contemplated, such as, for example, both members 620 and 621 being slideable along a substantially elastic or inelastic closure line 625.

The closure line 625 may be any biocompatible filament known in the art that is capable of securing the proximal occluder member 621 against the septum secundum 110 and septum primum 105. In a preferred embodiment the closure line 625 is a surgical suture, such as a multifilament non-biodegradable suture, or a forced entangled fiber filament. Alternatively, the closure line 625 may be made from an elastic material capable of exerting tension when stretched.

The proximal and distal members 621, 620 respectively, are expandable from a first, predeployed unexpanded configuration to a second expanded configuration. The expandable members 620, 621 are preferably constructed from a structurally deformable material.

Structurally deformable materials are materials that can elastically or plastically deform without compromising their integrity. Geometric structures, such as proximal and distal members 621, 620, made from a deformable material are capable of changing shape when acted upon by an external force, or removal or an external force.

Geometric structures made from structurally deformable materials are typically self expanding or mechanically expandable. In a preferred embodiment, the proximal and distal members 621, 620 made from a self-expanding material, such as Nitinol or a resilient polymer. However, the self-expanding members 621, 620 may also be made from elastically compressed spring temper biocompatible metals. These self-expanding structures are held in a constrained configuration by an external force, typically a capture sheath, and elastically deform when the constraining force is released.

Some structurally deformable materials may also be mechanically expandable. Geometric structures can be mechanically expanded by introduction of an external force, through, for example, a mechanical expansion means. Mechanical expansion means are well known in the art and include balloon or cage expansion devices.

Once an external mechanical force is introduced to the geometric structure, the structure plastically deforms to its desired final configuration.

The proximal and distal members 621, 620 in their constrained state are capable of being held in a restrained low profile geometry for delivery, and assume an expanded shape that facilitates the distal member 620 anchoring into the septal wall (septum secundum 110 or septum primum 105) and the proximal member 621 substantially covering and occluding the PFO track 120 entrance.

In a preferred embodiment, the proximal and distal members 621, 620 are cut from a Nitinol hypotube by methods known in the art.

Nitinol is utilized in a wide variety of applications, including medical device applications as described above. Nitinol or NiTi alloys are widely utilized in the fabrication or construction of medical devices for a number of reasons, including its biomechanical compatibility, its biocompatibility, its fatigue resistance, its kink resistance, its uniform plastic deformation, its magnetic resonance imaging compatibility, its ability to exert constant and gentle outward pressure, its dynamic interference, its thermal deployment capability, its elastic deployment capability, its hysteresis characteristics, and is moderately radiopaque.

Nitinol, as described above, exhibits shape memory and/or super-elastic characteristics. Shape memory characteristics may be simplistically described as follows. A metallic structure, for example, a Nitinol tube that is in an Austenitic phase may be cooled to a temperature such that it is in the Martensitic phase. Once in the Martensitic phase, the Nitinol tube may be deformed into a particular configuration or shape by the application of stress. As long as the Nitinol tube is maintained in the Martensitic phase, the Nitinol tube will remain in its deformed shape. If the Nitinol tube is heated to a temperature sufficient to cause the Nitinol tube to reach the Austenitic phase, the Nitinol tube will return to its original or programmed shape. The original shape is programmed to be a particular shape by well-known techniques.

Super-elastic characteristics may be simplistically described as follows. A metallic structure for example, a Nitinol tube that is in an Austenitic phase may be deformed to a particular shape or configuration by the application of mechanical energy. The application of mechanical energy causes a stress induced Martensitic phase transformation. In other words, the mechanical energy causes the Nitinol tube to transform from the Austenitic phase to the Martensitic phase. By utilizing the appropriate measuring instruments, one can determined that the stress from the mechanical energy causes a temperature drop in the Nitinol tube. Once the mechanical energy or stress is released, the Nitinol tube undergoes another mechanical phase transformation back to the Austenitic phase and thus its original or programmed shape. As described above, the original shape is programmed by well know techniques. The Martensitic and Austenitic phases are common phases in many metals.

Medical devices constructed from Nitinol are typically utilized in both the Martensitic phase and/or the Austenitic phase. The Martensitic phase is the low temperature phase. A material is in the Martensitic phase is typically very soft and malleable. These properties make it easier to shape or configure the Nitinol into complicated or complex structures. The Austenitic phase is the high temperature phase. A material in the Austenitic phase is generally much stronger than the material in the Martensitic phase. Typically, many medical devices are cooled to the Martensitic phase for manipulation and loading into delivery systems. When the device is deployed at body temperature, they return to the Austenitic phase.

Other materials that have shape memory characteristics may also be used, for example, some polymers and metallic composition materials. It should be understood that these materials are not meant to limit the scope of the invention.

Once the proximal and distal members 621, 620 are cut from the Nitinol hypotube, they are formed into a desired expanded configuration and annealed to assume a stress-free (relaxed) state. In one embodiment of the invention, the distal anchor member 620 is formed into an anchor shaped configuration, having a plurality of pointed legs with barbs 622 that can puncture and anchor in tissue. Correspondingly, in this embodiment, the proximal member 621 is formed into a slightly concaved woven-looking basket that could flatten into a woven-looking disc when pulled against the septal wall. An isomeric view of both the proximal and distal expandable members 621, 620, respectively, according to one embodiment of the present invention are illustrated in FIGS. 6A and 6B.

Once the closure device 600 is deployed, the distal anchor member 620 is anchored into septal wall (septum secundum 110 or septum primum 105) and the basket shaped occluder member 621 collapses under tensioning of the closure line 625, into a flattened disc shape as illustrated in FIGS. 6A and 6B. In this configuration, occluder member 621 is under strain. The super elastic properties of the occluder member 621 under strain exert an axially outward force against the adjacent tissue, putting the closure line 625 in tension.

This design should not be considered a limiting feature of the invention, as other shapes and configurations of proximal and distal members 621, 620 are also contemplated by the present design. These may include, for example, expandable disc design, star design, j-hook design, or any expandable symmetric or asymmetric geometric shape. In addition other materials exhibiting similar characteristics, such as non-biodegradable swellable polymers, are similarly contemplated by the present invention.

FIGS. 8A and 8B illustrate an asymmetric proximal member 621 according to another embodiment of the present invention. In the illustrated embodiment, the proximal member 621 is asymmetric about the hub incorporating locking mechanism 627. This asymmetry may allow the member 621 to more closely conform the shape of the surrounding tissue, taking advantage of the atrial anatomy.

Figure 9:
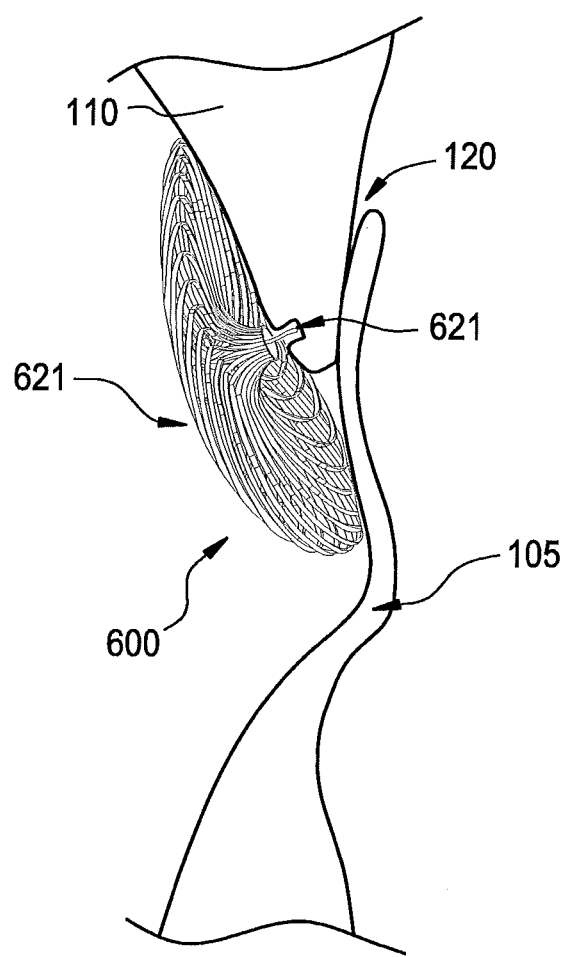
FIG. 9 illustrates a PFO closure device deployed to close a PFO track in the presence of an atrial septal defect according to one embodiment of the present invention.

The PFO closure device 600 can be used to facilitate closing the PFO track 120 when other defects in the septal wall are present. For example, the PFO closure device 600 may be used when an atrial septal aneurysm (ASA) is present. An ASA is characterized as a saccular deformity, generally at the level of the fossa ovale, which protrudes to the right or left atrium, or both. FIG. 9 illustrates the PFO closure device 600 deployed to close a PFO track 120 in the presence of an atrial septal defect.

The present invention utilizes a removable deployment device 630 to introduce the mechanical closure device 600 into the atrium of the heart, preferably through a minimally invasive, transluminal procedure.

FIGS. 10A and 10B are section views illustrating the closure device 600 loaded into a delivery device 630 according to two embodiments of the present invention. In each embodiment the delivery device 630 includes an outer tubular structure or catheter 635 and an inner tubular structure 636. The delivery device 630 may also include a guidewire lumen (not shown) to allow the delivery device 630 to track over a guidewire (not shown). The inner tubular structure 636 is slideably engaged within the outer tubular structure 635 and acts as a "pusher" to deploy the closure device 600 from the distal end of the outer tubular structure 635. In the embodiment illustrated in FIG. 10A, the inner tubular structure 636 is sized to push against the proximal end of the occluder 621, causing the occluder 621 to be displaced distally, and subsequently displacing the distal anchor member 620 from the distal end of the outer tubular structure 635. Similarly, in the embodiment illustrated in FIG. 10B, the inner tubular structure 636 is sized be slideably engaged with the proximal occluder 621, and to push against the proximal end of the distal anchor member 620, causing the distal anchor member 620 be displaced distally. As the distal anchor 620 is distally displaced, the proximal occluder member 621 is similarly displaced—by virtue of its relative position within the inner tubular structure 636, or alternatively, because it is operatively connected to the distal anchor ember 620 via the closure line 625.

Minimally invasive heart surgery refers to several approaches for performing heart operations that are less difficult and risky than conventional open-heart surgery. These approaches restore healthy blood flow to the heart without having to stop the heart and put the patient on a heart-lung machine during surgery. Minimally invasive procedures are carried out by entering the body through the skin, a body cavity or anatomical opening, but with the smallest damage possible to these structures. This results in less operative trauma for the patient. It also less expensive, reduces hospitalization time, causes less pain and scarring, and reduces the incidence of complications related to the surgical trauma, speeding the recovery.

One example of a minimally invasive procedure for performing heart surgery is a trans-thoracic laparoscopic (endoscopic) procedure. The part of the mammalian body that is situated between the neck and the abdomen and supported by the ribs, costal cartilages, and sternum is known as the thorax. This division of the body cavity lies above the diaphragm, is bounded peripherally by the wall of the chest, and contains the heart and lungs. Once into the thorax, the surgeon can gain access to the atrium of the heart through an atriotomy, a surgical incision of an atrium of the heart. For example, if the surgeon wishes to gain access to the right atrium they will perform an atriotomy in the right atrial appendage.

The primary advantage of a trans-thoracic laparosopic procedure is that there is no need to make a large incision. Instead, the surgeon operates through 3 or 4 tiny openings about the size of buttonholes, while viewing the patient's internal organs on a monitor. There is no large incision to heal, so patients have less pain and recover sooner. Rather than a 6- to 9- inch incision, the laparoscopic technique utilized only 4 tiny openings—all less than ½ inch in diameter.

Another minimally invasive technique for gaining access to the heart and deploying the closure device is a percutaneous transluminal procedure. Percutaneous surgical techniques pertain to any medical procedure where access to inner organs or other tissue is done via needle-puncture of the skin, rather than by using an "open" approach where inner organs or tissue are exposed (typically with the use of scalpel). The percutaneous approach is commonly used in vascular procedures, where access to heart is gained through the venous or arterial systems. This involves a needle catheter getting access to a blood vessel, followed by the introduction of a wire through the lumen of the needle. It is over this wire that other catheters can be placed into the blood vessel. This technique is known as the modified Seldinger technique. The PFO closure device 600 may also be deployed via percutaneous methods by steerable catheters or guidewires.

In the Seldinger technique a peripheral vein (such as a femoral vein) is punctured with a needle, the puncture wound is dilated with a dilator to a size sufficient to accommodate an introducer sheath, and an introducer sheath with at least one hemostatic valve is seated within the dilated puncture wound while maintaining relative hemostasis.

With the introducer sheath in place, the guiding catheter or delivery member of the closure device is introduced through the hemostatic valve of the introducer sheath and is advanced along the peripheral vein, into the region of the vena cavae, and into the right atrium.

By way of example, in one embodiment of the present invention, using right atrial access, the right atrium is first accessed by the delivery device (and closure device 600). The delivery device may be a catheter having a distal end specifically designed to hold the closure device 600, particularly the distal anchor member 620 and proximal occluder member 621 in a radially collapsed position. As previously described, FIGS. 10A and 10B illustrate two embodiments of the closure device 600 stored in the delivery device 630 as a payload for delivery.

Figure 11:
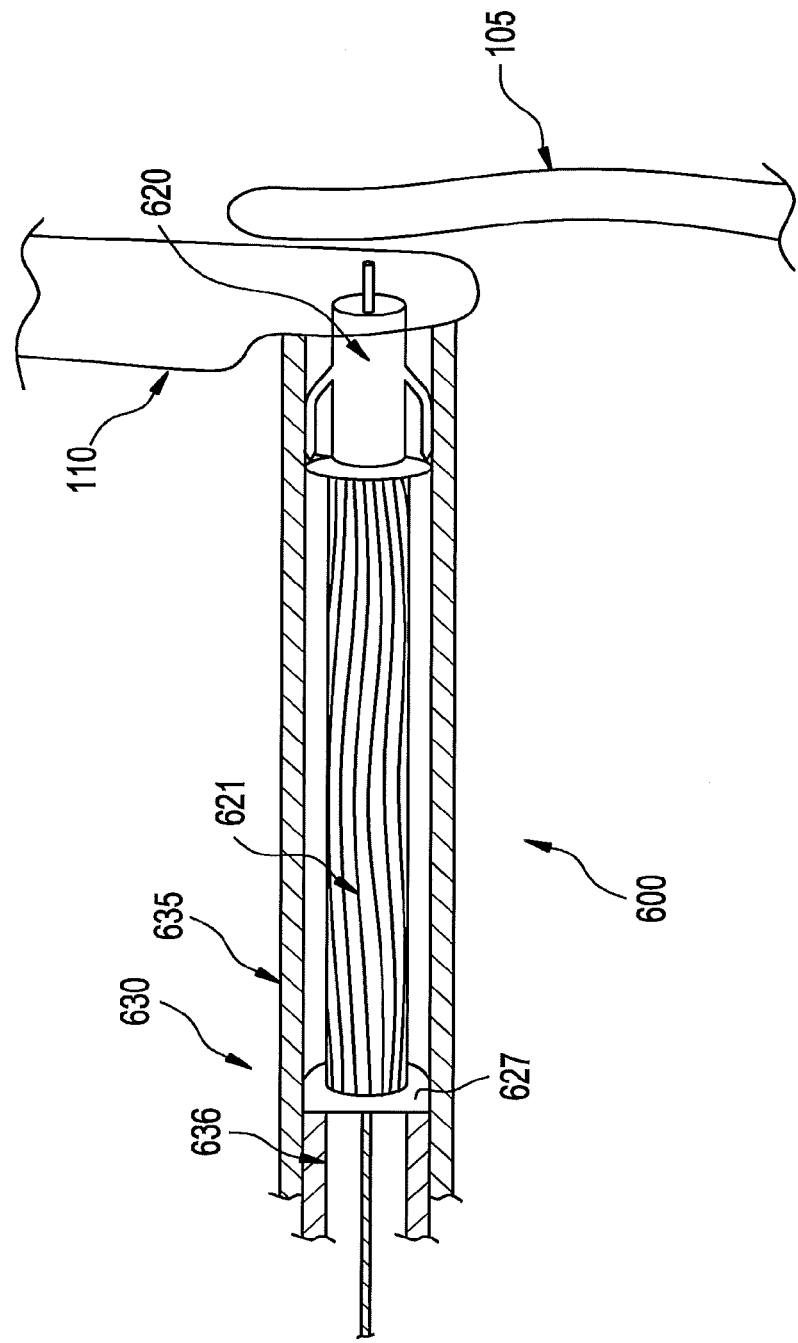
FIG. 11 is a perspective view illustrating the closure device, wherein the distal anchor member is initially set in the septum secundum according to one embodiment of the present invention.

The closure device 600 may then be deployed by first inserting the distal anchor member 620 into the septal tissue of either the septum secundum 110 or septum primum 105 and deploying the distal anchor member 620 associated with the closure device 600 into the tissue. As previously disclosed, initial deployment of the distal anchor member 620 may be by distally displacing the inner tubular structure 636 relative to the outer tubular structure 635. FIG. 11 is a perspective view illustrating the closure device 600 wherein the distal anchor member 620 is initially set in the septum secundum 110 according to one embodiment of the present invention.

Figure 12:
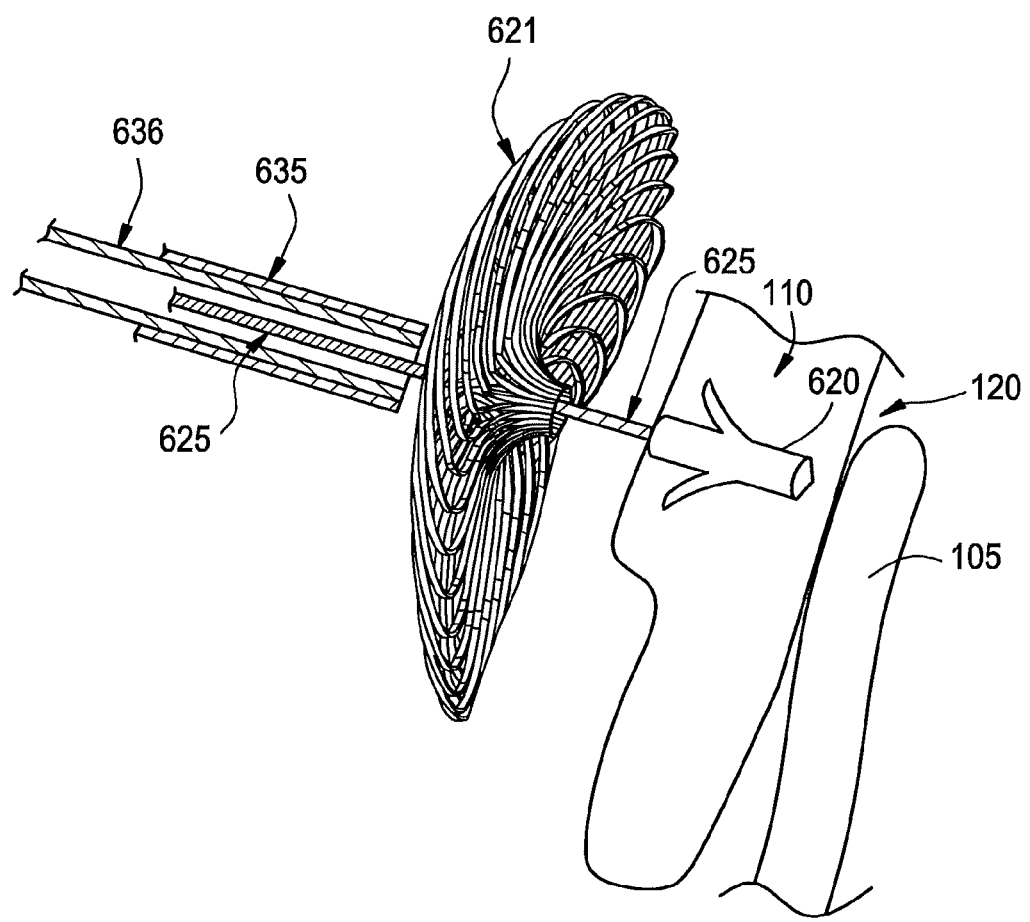
FIG. 12 illustrates the closure device in a substantially deployed configuration according to one embodiment of the present invention.

After successful deployment of the distal anchor member 620, the delivery device 630 may be withdrawn from the septal wall into the right atrial chamber, leaving the distal anchor member 620 in place. The proximal occluder member 621 associated with the closure device 600 can then be deployed into the right atrial chamber. This may be achieved by the continued distal displacement of the inner tubular structure 636 relative to the outer tubular structure 635, or by simple retraction of the delivery device 630. FIG. 12 illustrates the closure device 600 in a substantially deployed configuration according to one embodiment of the present invention.

Figure 13:
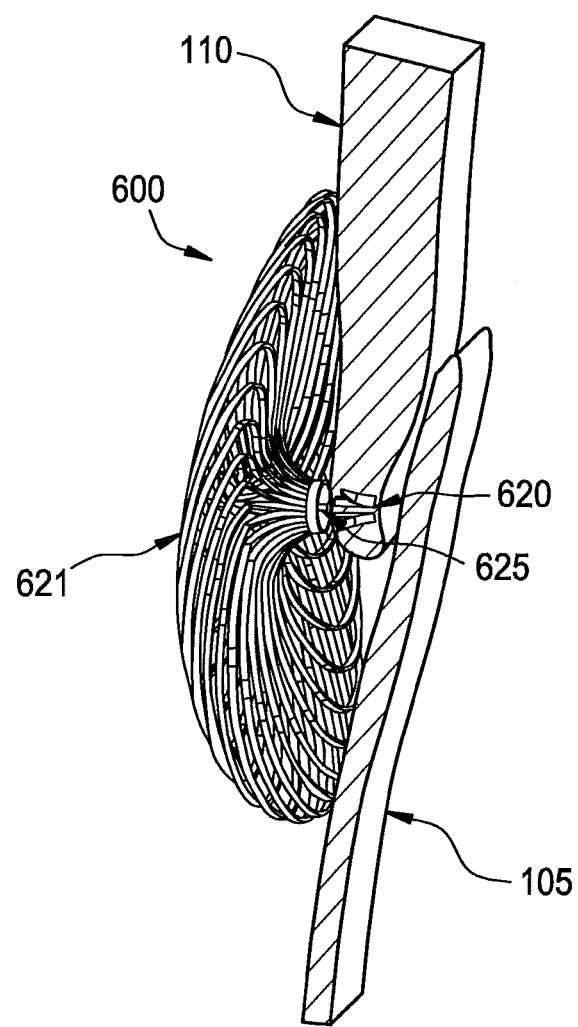
FIG. 13 is a perspective view of the closure device according to one embodiment of the present invention cinched in place.

Once the proximal occluder member 621 is deployed, the closure device 600 may be cinched to bring the proximal occluder member 621 against the septal wall, which is comprised of the septum secundum 110 and the septum primum 105. This results in the proximal occluder member 621 being compressed against the septal wall, covering over the PFO tunnel entrance 120, and substantially occluding or blocking blood flow to the tunnel, resulting in "closure" of the Patent Foramen Ovale. Cinching may be performed by tensioning the closure line 625 i.e. by proximally displacing the closure line 625 relative to the proximal occluder member 621. FIG. 13 is a perspective view of the closure device 600 according to one embodiment of the present invention cinched in place.

It should be noted that the proximal occluder member 621 may or may not be coated or covered with a biocompatible polymeric fabric that could assist in occluding blood flow into the tunnel. In the case that the proximal occluder member 621 is not covered, blood flow shunting through the PFO track 120 might not decrease as rapidly as it would in the covered case, however eventually the incorporation of the proximal occluder 621 would block a sufficient amount of flow such that the PFO track (tunnel) 120 would be substantially closed or considered closed.

To achieve and maintain the proximal occluder member 621 against the septum secundum 110 and the septum primum 105, it may be necessary to adjust the proximal occluder member 621 by uni-axially cinching or sliding the proximal member 621 along closure line 625. In one embodiment of the invention, cinching comprises uni-axially adjusting the proximal occluder member 621 relative to a closure line 625 associated with the closure device 600. In another embodiment of the invention, cinching comprises incrementally adjusting the proximal occluder member 621 relative to a closure line 625 associated with the closure device 600.

Once the closure device 600 is cinched in place the method may further comprise assessing the degree of blockage of the PFO track 120.

In one embodiment of the invention, the clinician may visually assess the proximation though an endoscopic or fluoroscopic procedure. In addition, other methods may be used to measure the blockage or closure of the PFO track 120, such as through pressure observation or infrared imaging.

After proper cinching, any unwanted length of closure line 625 that remains unconstrained within the right atrium may be mechanically removed. Devices known in the art capable of removing the excess closure line 625 include catheter-based snare and cut devices. In addition to independent devices, a mechanical cut and removal mechanism may be integrated into the deployment device.

The closure device 600 will then be in position, with the anchor member 620 open and anchored in the septal wall (septum secundum 110 or septum primum 105), with the proximal occluder member 621 flattened against the septum secundum 110 and/or septum primum 105, and the closure line 625 connecting the proximal and distal expandable members 621, 620, respectively, thus holding the proximal occluder member 621 against the septal wall.

Another embodiment of the invention may include a location monitoring system to facilitate placement of the deployment device 630. In particular, the location monitoring device will assist in determining whether the clinician is in the correct chamber of the heart.

In a preferred embodiment, the location monitoring system includes the ability to measure localized pressure relative to the distal end of the deployment device 630. The pressure measurement read by the location monitoring system may be achieved by electronic, mechanical and/or physical means, such as a solid-state pressure transducer, spring loaded diaphragm, hydraulic pressure port, and/or communicating manometer. These and other pressure measurement techniques would be known by one of skill in the art.

By way of example it is well known that pressures vary in different locations within the cardiovascular system. Specifically, gage pressure in the right and left atrium are know to range from approximately 1-6 mmHg to 10 mmHg respectfully. Similarly, gage pressure within the ascending aorta ranges from approximately 120 to 160 mmHg during systole.

For delivery to the heart, the deployment device 630 (and thus the closure device 600) is used in conjunction with an accessory device (not shown) known in the art. In a preferred embodiment, the accessory device may be a guiding catheter that tracks over a guidewire, and is steered through the vasculature into the right atrium.

In another embodiment, the accessory device and deployment device 630 may be formed as an integrated component, capable of being steered through the vasculature.

Figure 14A:
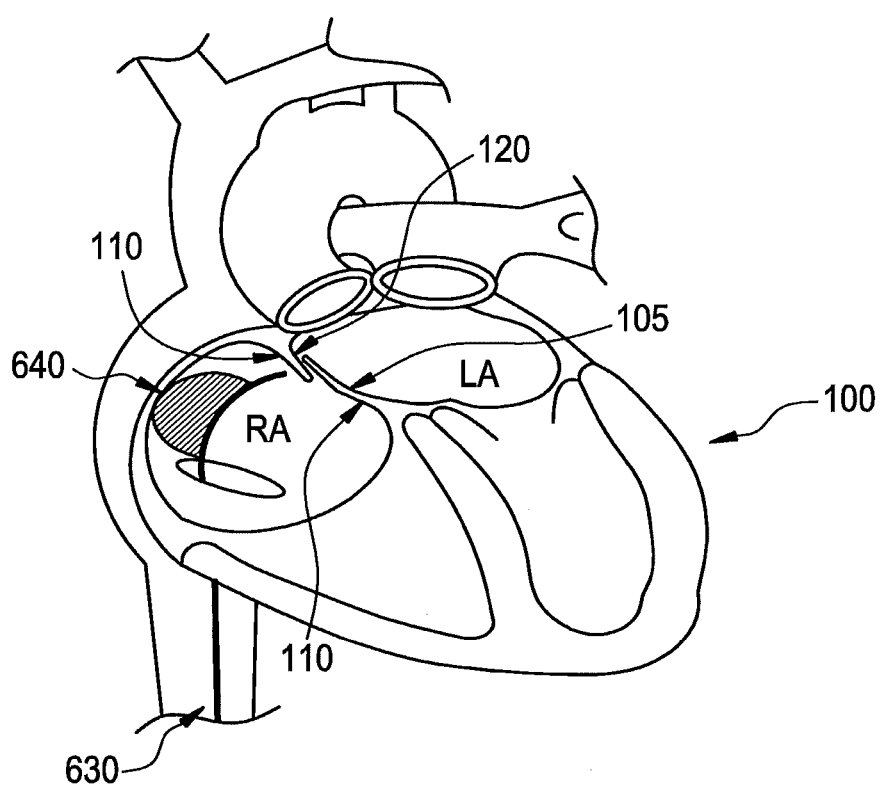
FIG. 14A is a section view of a heart illustrating the location of a delivery device having an axially asymmetric expansion member as backup support feature according to one embodiment of the present invention.
Figure 14B:
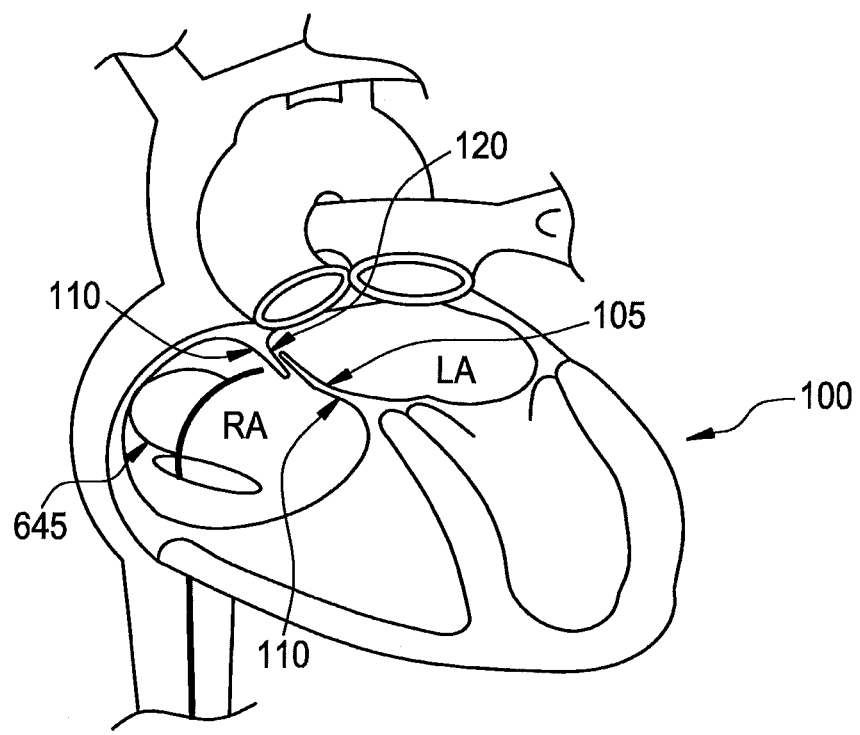
FIG. 14B is a section view of a heart illustrating the location of a delivery device having a spine member as a backup support feature according to one embodiment of the present invention.
Figure 14C:
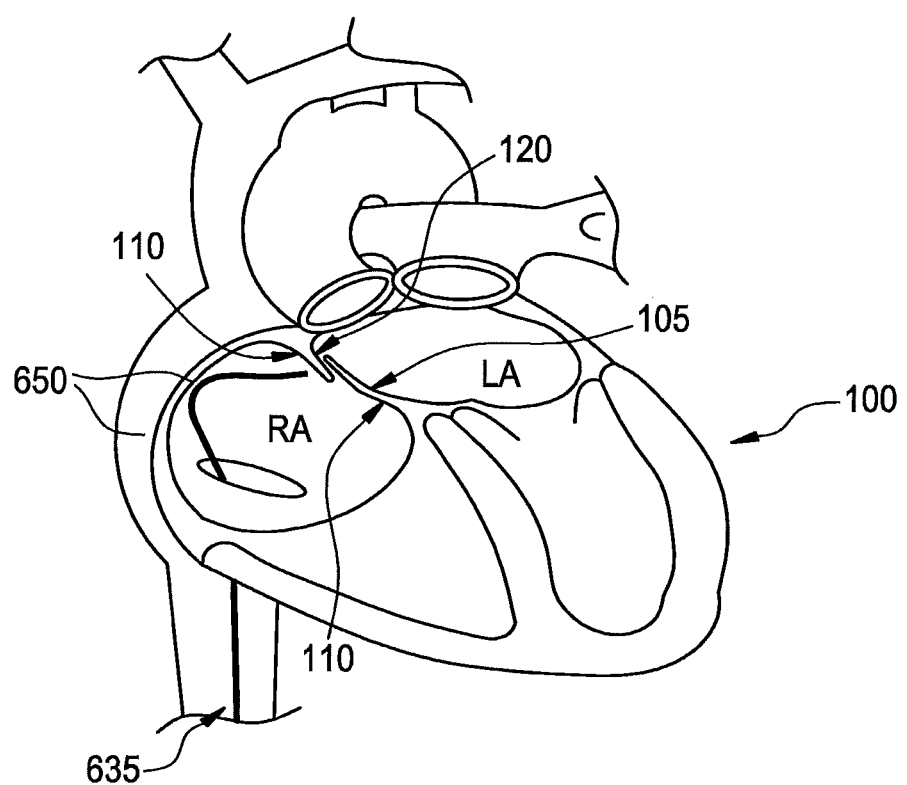
FIG. 14C is a section view of a heart illustrating the location of a delivery device having a shaped member as a backup support feature according to one embodiment of the present invention.

To facilitate deployment of the closure device 600, the deployment device 630 may include features that provide backup support. This backup support may include, for example: an axially asymmetric expansion member attached along an outer shaft (outer tubular structure) 635, such as a balloon or self expanding cage 640; a spline 645; or imparting a shape 650 along the body of the deployment device 630. Examples of these backup support features are illustrated in FIGS. 14A through 14C, respectively. It should be understood that the outer shaft 635 may be part of the guiding catheter, or integrated into the deployment device 630. These and other such backup support devices would be understood by one of skill in the art. These backup support features can also be incorporated onto accessory devices, such as the guide catheter.

Still other embodiments utilizing known methods and apparatus to deliver the deployment device 630 and closure device 600 into the atrium of heart 100 would be obvious to one of skill in the art.

What is claimed is:

1. A method of closing a persistent passageway in a heart between a septum primum and septum secundum, the passageway having a first and a second open end, comprising:
    locating a distal end of a closure device adjacent to the persistent passageway, the closure device having a closure line with proximal and distal ends, an expandable tissue anchor located along the distal end of the closure line, and an expandable occluder member located along the proximal end of the closure line;
    deploying the expandable tissue anchor into a septal tissue of only one of the septum primum and septum secundum adjacent to the persistent passageway;
    deploying the expandable occluder member adjacent to the persistent passageway by piercing a surface of the tissue with the expandable tissue anchor and expanding the tissue anchor within the septal tissue without the anchor detaching from the septal tissue such that the expandable occluder member substantially covers the second opening to the persistent passageway.

2. The method of claim 1 wherein deploying the expandable occluder member adjacent to the passageway comprises expanding the occluder member from a first configuration to a second configuration, and tensioning the occluder against the tissue to substantially cover the persistent passageway.

3. The method of claim 2 wherein tensioning the occluder against the tissue comprises unilaterally displacing the occluder distally along the closure line.

* * * * *